US008962795B2

(12) United States Patent
Lambris

(10) Patent No.: US 8,962,795 B2
(45) Date of Patent: Feb. 24, 2015

(54) FACTOR H BINDING PEPTIDES AND USES THEREOF

(75) Inventor: John D. Lambris, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/994,485

(22) PCT Filed: Dec. 19, 2011

(86) PCT No.: PCT/US2011/065822
§ 371 (c)(1),
(2), (4) Date: Sep. 9, 2013

(87) PCT Pub. No.: WO2012/087925
PCT Pub. Date: Jun. 28, 2012

(65) Prior Publication Data

US 2013/0344592 A1 Dec. 26, 2013

Related U.S. Application Data

(60) Provisional application No. 61/425,074, filed on Dec. 20, 2010.

(51) Int. Cl.
*C07K 7/64* (2006.01)
*A61K 38/12* (2006.01)
*A61P 37/00* (2006.01)
*A61L 33/12* (2006.01)
*C07K 7/06* (2006.01)
*C07K 7/08* (2006.01)
*A61K 38/00* (2006.01)

(52) U.S. Cl.
CPC ................. *C07K 7/64* (2013.01); *A61L 33/128* (2013.01); *C07K 7/06* (2013.01); *C07K 7/08* (2013.01); *A61K 38/00* (2013.01); *A61L 2300/25* (2013.01)
USPC .......................................... 530/317; 514/21.1

(58) Field of Classification Search
CPC .............. C07K 7/64; C07K 7/08; C07K 7/06; A61K 38/00; A61L 33/128; A61L 2300/25
See application file for complete search history.

(56) References Cited

U.S. PATENT DOCUMENTS

2003/0199671 A1* 10/2003 Rondon et al. ................ 530/317

FOREIGN PATENT DOCUMENTS

WO 02/08426 1/2002
WO 2010/028096 3/2010

OTHER PUBLICATIONS

Nilsson et al, Autoregulation of thromboinflammation on biomaterial surfaces by a multicomponent therapeutic coating, Biomaterials, 2013, 34, pp. 985-994.*

Nilsson et al., "The creation of an antithrombotic surface by apyrase immobilization", *Biomaterials*, 2010; 31:4484-4491.

Andersson et al., "Binding of a Model Regulator of Complement Activation (RCA) to a Biomaterial Surface: Surface-Bound Factor H Inhibits Complement Activation", *Biomaterials*, 2001; 22:2435-2443.

Andersson et al., "C3 Adsorbed to a Polymer Surface Can Form an Initiating Alternative Pathway Convertase," 2002, *J Immunol*, 168:5786-5791.

Andersson et al., "Surface-Attached PEO in the Form of Activated Pluronic With Immobilized Factor H Reduces Both Coagulation and Complement Activation in a Whole-Blood Model", *J. Biomed. Mater. Res. A.*, 2005; 76:25-34.

Andersson et al., "Binding of C3 Fragments on Top of Adsorbed Plasma Proteins During Complement Activation on a Model Biomaterial Surface", *Biomaterials*, 2005, 26:1477-1485.

Collier et al., "Protein Adsorption on Chemically Modified Surfaces", *Biomed. Sci. Instrum.*, 1997; 33:178-183.

Engberg et al., "Inhibition of Complement Activation on a Model Biomaterial Surface by Streptococcal M Protein-Derived Peptides", *Biomaterials*, 2009; 30(13):2653-2659.

Engstad et al., "Modulation of Blood Cell Activation by Four Commonly Used Anticoagulants", *Thromb. Haemost.*, 1997; 77:690-696.

Harboe et al,, "The Quantitative Role of Alternative Pathway Amplification in Classical Pathway Induced Terminal Complement Activation", *Clin. Exp. Immunol.*, 2004; 138:439-446.

Huebsch et al., "Inspiration and Application in the Evolution of Biomaterials", *Nature*, 2009; 462:426-432.

Jozsi et al., "Factor H Family Proteins and Human Diseases", *Trends Immunol.*, 2008; 29:380-387.

Korsgren et al., "Improving Islet Transplantation: A Road Map for a Widespread Application for the Cure of Persons With Type I Diabetes", *Curr Opin Organ Transplant*, 2009; 14:683-687.

Kourtzelis et al., "Complement Anaphylatoxin C5a Contributes to Hemodialysis-Associated Thrombosis", *Blood*, 2010;116:631-639.

Krishna et al., "Protein- and Peptide-Modified Synthetic Polymeric Biomaterials", *Peptide Science*, 2010; 94:32-48.

Lambris et al., "Complement Evasion by Human Pathogens", *Nat. Rev. Microbiol.*, 2008; 6:132-142.

Lappegard et al., "Effect of Complement Inhibition and Heparin Coating on Artificial Surface-Induced Leukocyte and Platelet Activation," *Ann Thorac Surg.*, 2004; 77:932-941.

Lappegard et al., "Differential Effect of Heparin Coating and Complement Inhibition on Artificial Surface-Induced Eicosanoid Production," *Ann. Thorac. Surg.*, 2005; 79:917-923.

Lhotta et al., "Rapid Activation of the Complement System by Cuprophane Depends on Complement Component C4," *Kidney Int.*, 1998; 53:1044-1051.

Liu et al., "Complement Activation on Solid Surfaces as Determined by C3 Deposition and Hemolytic Consumption," *J. Biomed. Mater. Res.*, 1994; 28:767-773.

(Continued)

*Primary Examiner* — Julie Ha
*Assistant Examiner* — Li Ni Komatsu
(74) *Attorney, Agent, or Firm* — Potter Anderson and Corroon LLP

(57) ABSTRACT

Factor H-binding peptides that binds to a region of factor H that does not impede the complement-inhibitory activity of factor H are disclosed. When immobilized onto the surface of a biomaterial, these peptides recruit factor H, resulting in a substantial inhibition of biomaterial-induced complement activation in a biological substance exposed to the biomaterial.

16 Claims, 6 Drawing Sheets

(56) References Cited

OTHER PUBLICATIONS

Mollnes et al., "Essential role of the C5a Receptor in *E coli*-Induced Oxidative Burst and Phagocytosis Revealed by a Novel Lepirudin-Based Human Whole Blood Model of Inflammation," *Blood*, 2002;100:1869-1877.

Nilsson et al., "Compstatin Inhibits Complement and Cellular Activation in Whole Blood in Two Models of Extracorporeal Circulation," *Blood*, 1998,92: 1661-1667.

Nilsson et al., "The Role of Complement in Biomaterial-Induced Inflammation," *Mol. Immunol.*, 2007; 44: 82-94.

Nilsson et al., "Can Cells and Biomaterials in Therapeutic Medicine be Shielded Off From Innate Immune Recognition?," *Trends Immunol.*, 2010;31:32-38.

Okemefuna et al., "Electrostatic Interactions Contribute to the Folded-Back Conformation of Wild Type Human Factor H,"*J. Mol. Biol.*, 2009; 98-118.

Oppermann et al., "The C-Terminus of Complement Regulator Factor H Mediates Target Recognition: Evidence for a Compact Conformation of the Native Protein," *Clin. Exp. Immunol.*, 2006; 144:342-352.

Pickering et al., "Translational Mini-Review Series on Complement Factor H: Renal Diseases Associated With Complement Factor H: Novel Insights From Humans and Animals," *Clin. Exp. Immunol.*, 2008; 151:210-230.

Prosser et al., "Structural Basis for Complement Factor H Linked Age-Related Macular Degeneration," *J. Exp. Med.*, 2007; 204:2277-2283.

Ratner, "The Catastrophe Revisited: Blood Compatibility in the 21st Century, "*Biomaterials*, 2007; 28:5144-5147.

Ricklin et al., "Complement: a key System for Immune Surveillance and Homeostasis", *Nat. Immunol.*, 2010; 11:785-797.

Ricklin et al., "Compstatin: a Complement Inhibitor on its way to Clinical Application", *Adv. Exp. Med. Biol.*, 2008; 632:273-292.

Rosengren et al., "Plasma Protein Adsorption Pattern on Characterized Ceramic Biomaterials", *Biomaterials*, 2002; 23:1237-1247.

Ross et al., "Generation of Three Different Fragments of Bound C3 With Purified Factor I or Serum. I. Requirements for Factor H vs CR1 Cofactor Activity", *J. Immunol.*, 1982; 129:2051-2060.

Sahu et al., "Inhibition of Human Complement by a C3-Binding Peptide Isolated From a Phage-Displayed Random Peptide Library", 1996,*J. Immunol.*, 157:884-891.

Schmidt et al., "Inhibitor of Complement, Compstatin, Prevents Polymer-Mediated Mac-1 Up-Regulation of Human Neutrophils Independent of Biomaterial Type Tested", *J. Biomed. Mater. Res. A.*, 2003; 66:491-499.

Schmidt et al., "A new map of Glycosaminoglycan and C3b Binding Sites on Factor H", J Immunol., 2008;181:2610-2619.

Schmidt et al., "Translational Mini-Review Series on Complement Factor H: Structural and Functional Correlations for Factor H", *Clin. Exp. Immunol.*, 2008; 151:14-24.

Schmidt et al., "The Central Portion of Factor H (modules 10-15) is Compact and Contains a Structurally Deviant CCP Module", *J. Mol. Biol.*, 2010; 395:105-122.

Sperling et al., "In Vitro Blood Reactivity to Hydroxylated and Non-Hydroxylated Polymer Surfaces", *Biomaterials*, 2007; 28:3617-3625.

Tengvall et al., "Complement Activation by 3-Mercapto-1,2-Propanediol Immobilized on Gold Surfaces", *Biomaterials*, 1996; 17:1001-1007.

Watkins et al., "Coating of Human Decay Accelerating Factor (hDAF) onto Medical Devices Improves Biocompatibility", *Immunopharmacology*, 1997, 38:111-118.

Williams, D F, "On the Nature of Biomaterials", *Biomaterials*, 2009; 30:5897-5909.

Wu et al., "Structure of C3b-Factor H and Implications for Host Protection by Complement Regulators", *Nat. Immunol.* , 2009, 10:728-733.

Wu et al., "Protection of nonself surfaces from complement attack by factor H-binding peptides: implications for therapeutic medicine", *J. Immunol.*, 2011, 186:4269-4277.

International Search Report and Written Opinion of the International Searching Authority in PCT/US2011/065822, issued Jun. 13, 2012.

* cited by examiner

FACTOR H BINDING PEPTIDES AND USES THEREOF

This is a United States national stage, pursuant to 35 U.S.C. §371, of International Application No. PCT/US2011/065822, filed Dec. 19, 2011, which claims benefit of U.S. Provisional Application No. 61/425,074, filed Dec. 20, 2010, the entire contents of each of which are incorporated by reference herein.

This invention was made with government support under Grant Nos. EB003968, AI060687 and AI030040 awarded by the National Institutes of Health. The government has certain rights in the invention.

FIELD OF THE INVENTION

This invention relates to the field of inhibition of complement activation. In particular, the invention provides factor H-binding peptides that bind to a region of factor H that does not impede the complement-inhibitory activity of factor H.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

Therapeutic medicine increasingly relies on applications involving artificial or non-self surfaces, like the implantation or extracorporeal use of biomaterials (e.g., hemodialysis filters, medical devices, and drug delivery systems) or the transplantation of cell clusters (e.g., Langerhans islets) (Huebsch, N & D J Mooney, 2009, *Nature* 462:426-432; Williams, D F, 2009, *Biomaterials* 30:5897-5909; Korsgren, O & B Nilsson, 2009, *Curr Opin Organ Transplant* 14:683-687). Although considerable progress has been made in improving the biocompatibility of such non-self materials, their use in medical applications is still hampered by adverse reactions related to the activation of innate immunity and pro-inflammatory pathways; the level of inflammation and associated tissue damage can range from moderate to lethal for the patient (Nilsson, B, O Korsgren, et al., 2010, *Trends Immunol* 31:32-38; Ratner, B D, 2007, *Biomaterials* 28:5144-5147). By using soluble complement inhibitors (i.e., compstatin, Sahu, A et al., 1996, *J Immunol* 157:884-891; Ricklin, D & J D Lambris, 2008, *Adv Exp Med Biol* 632:273-292) or coating surfaces with heparin, several groups showed that inhibition of complement activation largely attenuates biomaterial-induced activation and surface adhesion of cells (Lappegard, K T et al., 2005, *Ann Thorac Surg* 79:917-923; Schmidt, S, G et al., 2003, *J Biomed Mater Res A* 66:491-49910; Nilsson, B, R et al., 1998, *Blood* 92:1661-1667; Engstad, C S et al., 1997, *Thromb Haemost* 77:690-696). These observations clearly demonstrate that activation of the complement cascade on biomaterials or cell clusters, and the subsequent cross-talk with cytokine and coagulation pathways, marks a major cause of detrimental inflammatory responses (Nilsson, B, K et al., 2007, *Mol Immunol* 44:82-94). In particular, the anaphylatoxin C5a is known to potently attract immune cells and trigger their activation, whereas surface-bound C3b is responsible for cell adhesion (Sperling, C et al., 2007, *Biomaterials* 28:3617-3625; Mollnes, T E et al., 2002, *Blood* 100:1869-1877). Very recently, the beneficial impact of complement inhibition in clinical biomaterial application was impressively demonstrated for the case of hemodialysis, where addition of compstatin to blood not only inhibited filter-induced complement response but also the subsequent activation of immune cells and the expression of pro-coagulative factors (Kourtzelis, I et al., 2010, *Blood* 116:631-639). Yet for many applications a continuous administration of soluble inhibitors is not feasible, making modified surfaces with direct autoregulatory activity highly desired.

Recent data indicate that foreign surfaces rapidly adsorb abundant plasma proteins such as human serum albumin (HSA), IgG, and fibrinogen upon contact with blood or tissue, thereby forming an initial monolayer of proteins (Rosengren, A et al., 2002, *Biomaterials* 23:1237-1247; Collier, T O et al., 1997, *Biomed Sci Instrum* 33:178-183; Andersson, J et al., 2005, *Biomaterials* 26:1477-1485) on which complement activation occurs (Andersson, J et al., 2002, *J Immunol* 168:5786-5791; Liu, L & H Elwing, 1994, *J Biomed Mater Res* 28:767-773). Whereas the classical pathway is likely to be involved in the initiation of the cascade (Lhotta, K, R et al., 1998, *Kidney Int* 53:1044-1051; Tengvall, P et al., 1996, *Biomaterials* 17:1001-1007), e.g., via recognition of adsorbed IgG by C1q, the alternative pathway (AP) appears to be the driving force behind the overall response. For one, adsorption of C3 to the protein layer may induce transformations that enable the formation of initial C3 convertases. Moreover, nascent C3b generated by either pathway binds to HSA and IgG (but not fibrinogen) in the protein layer, thereby leading to the assembly of the main AP convertase, C3bBb, and rapid amplification of complement response (Nilsson, B, K et al., 2007, supra: Andersson, J et at, 2005, supra). The contribution of direct AP activation is further underscored by the observation that hemodialysis treatment of C4-deficient patients can induce complement activation, although at a slower rate compared to complement sufficient individuals (Lhotta, K, R et al., 1998, supra; Lappegard, K T et al., 2004, *Ann Thorac Surg* 77:932-941). Further, it has been reported that the AP may contribute more than 80% of the C5a and terminal complement complex, C5b-9, that is produced during complement response (Harboe, M, G et al., 2004, *Clin Exp Immunol* 138:439-446). This observation suggests that the effector phase of complement, following recognition by the CP or the lectin pathway (LP) is indeed dependent on AP-mediated amplification.

Thus, the AP plays a role in the complement-related incompatibility of non-self materials and is considered a suitable target for inhibition aimed at increasing the biocompatibility of these materials. Under homeostatic conditions, complement activation is tightly and precisely controlled by membrane-bound and soluble regulators of complement activation (RCA) (Lambris, J D et al., 2008, *Nat Rev Microbial* 6:132-142; Ricklin, D et al., 2010, *Nat Immunol* 11:785-797). Factor H, the second most abundant complement protein in plasma, is the primary regulator of the AP. It is has an elongated structure consisting of 20 homologous short consensus repeats (SCR), each comprising approximately 60 amino acids held together by four conserved cysteine residues. Whereas the complement regulatory functions are concentrated to the N-terminus (SCR 1-4) of factor H, two distinct regions (SCR 7, SCR 19-20) define the recognition of self-surfaces via binding to polyanion patches (e.g., glycosaminoglycans; GAG) on host cells. Factor H regulates the AP by inhibiting the formation of the AP C3 convertase and accelerating its dissociation, or by acting as cofactor for the degradation of C3b by factor I (Wu, J et al., 2009, *Nat Immunol* 10:728-733; Schmidt, C et al., 2008, *J Immunol* 181:2610-2619; Schmidt, C et al., 2008, *Clin Exp Immunol* 151:14-24; Pickering, M C et al., 2008, *Clin Exp Immunol* 151:210-230; Jozsi, M, & P F Zipfel, 2008, *Trends Immunol* 29:380-387;

Ross, G D et al., 1982, *J Immunol* 129:2051-2060). In the fluid phase, factor H was reported to have a bent or hairpin-like, rather than a linear structure (Schmidt, C Q et al., 2010, *J Mol Biol* 395:105-122; Okernefuna, A I et al., 2009, *J Mot Biol* 391:98-118; Prosser, 13 E et al., 2007, *J Exp Med* 204: 2277-2283; Oppermann, M, T et al., 2006, *Clin Exp Immunol* 144:342-352).

Surface coating with modulatory proteins or peptides is an approach for increasing biomaterial biocompatibility (Nilsson, P H et al., 2010, *Biomaterials* 31:4484-4491; Krishna, O D, & K L Kiick, 2010, 94:32-48). Theoretically, biomaterial surface-immobilized RCA proteins should confer a complement-regulatory capacity on the surface and increase its biocompatibility. Indeed, immobilization of the AP regulators factor H and decay accelerating factor (CD55) both attenuated biomaterial-induced complement in previous studies (Andersson, J et al., 2001, *Biomaterials* 22:2435-2443; Watkins, N J et al., 1997, *Immunopharmacology* 38:111-118; Andersson, J et al., 2006, *J Biomed Mater Res A* 76:25-34). However, although feasible to perform on a laboratory scale, the preparation and immobilization of the large RCA proteins is costly and likely associated with great loss of function. As a consequence, this approach would hardly be practical on a commercial scale. An alternative way to increase the blood compatibility of a surface is to conjugate molecules (e.g., antibodies or peptides) with affinity for a plasma protein like factor H or C4b-binding protein (C4BP). The aim for such a procedure is that the structure on the surface should capture its ligand, ideally in an active conformation, when exposed to blood, recruiting a soluble RCA to the artificial surface. Notably, several human pathogens employ recruitment of host regulators as part of their immune evasion strategy (Lambris, J D et al., 2008, supra). A first attempt to utilize this approach for creating a complement-autoregulatory surface was made by Engberg et al., who reported that surface coating with C4BP-binding peptides from *Streptococcus pyogenes* inhibited complement activation via the CP on a model biomaterial surface (Engberg, A E et al., 2009, *Biomaterials* 30:2653-2659). Clearly, there is a need for development of additional systems of this type. The present invention satisfies that need.

SUMMARY OF THE INVENTION

One aspect of the invention features a peptide that binds factor H without interfering with a biological activity of factor H comprising inhibiting complement activation. The peptide can inhibit complement activation by down-regulating the alternative pathway (AP) of complement activation; in particular, by inhibiting formation of the AP C3 convertase. In certain embodiments, the peptide binds factor H in one or more of short consensus repeats (SCR) 5-18. The peptide can be any suitable size, and typically is less than about 20 amino acid residues in length; more specifically, less than about 15 amino acid residues in length.

In certain embodiments, the aforementioned peptide can be represented by Formula I:

Z—U    Formula I wherein:

U is a cysteine cyclic peptide comprising: Cys-Xaa1-Tyr-Xaa2-Xaa3-Trp-Cys-Xaa4-His (SEQ ID NO:1)

wherein:

Xaa1 is any amino acid;

Xaa2 is Asp or Ser;

Xaa3 is His or Tyr; and

Xaa4 is any amino acid; and

Z is absent or is a peptide comprising: Ala-Ser-Xaa5-Xaa6-Xaa7 (SEQ ID NO:2)

wherein:

Xaa5 is Ser or Pro;

Xaa6 is absent or is any amino acid; and

Xaa7 is absent or is any amino acid;

wherein Z, if present, and U are joined by a peptide bond. In certain embodiments, Xaa1 is Thr, Ser, Asp or Met. In certain embodiments, Xaa4 is Ser, Arg, Leu, Ala or Thr. In certain embodiments, Xaa6 is Ser, Phe or Asn. In certain embodiments, Xaa7 is Arg, Trp, Lys or Val. In particular embodiments, the peptide comprises a sequence selected from: ASSSRCTYDHWCSH (SEQ ID NO:3); ASPSWCSYSHWCRH (SEQ ID NO:4); ASSFKCDYSHWCLH (SEQ ID NO:5); ASSNVCSYSYWCAH (SEQ ID NO:6); and ASSCMYSYWCTH (SEQ ID NO:7).

Another aspect of the invention features a composition comprising the above-described factor H-binding peptide affixed to a biomaterial. In various embodiments, the biomaterial comprises one or more of polymers, plastics, metals, ceramics, artificial tissues and organs, or living cells, tissues and organs. In certain embodiments, the peptide is irreversibly affixed to the biomaterial, while in other embodiments, the peptide is reversibly affixed to the biomaterial.

Another aspect of the invention features a method of reducing complement activation in a biological substance that is exposed to a biomaterial, the method comprising: (1) affixing to the biomaterial a peptide that binds factor H without interfering with the ability of the factor H to inhibit complement activation thereby forming a peptide-coated biomaterial; (2) contacting the peptide coated biomaterial with factor H, whereupon the factor H is bound to the peptide on the peptide-coated biomaterial, thereby forming a factor H-enriched biomaterial; and (3) exposing the biological substance to the factor H-enriched biomaterial, whereupon the complement activation in the exposed biological substance is reduced in comparison to an equivalent biological substance exposed to an equivalent biomaterial that has not been affixed with the peptide and contacted with the factor H.

In certain embodiments, e.g., when the biological substance is a factor H-containing fluid, such as blood or a component of blood, or lymph or a component of lymph, or intramuscular fluid, the biological substance contains the factor H, and the contacting can be accomplished when the biological substance is exposed to the peptide-coated biomaterial. In other embodiments, e.g., when the biological substance is a tissue or organ, the contacting can be performed before the biological substance is exposed to the peptide-coated biomaterial.

Other features and advantages of the invention will be understood by reference to the drawings, detailed description and examples that follow.

DETAILED DESCRIPTION OF ILLUSTRATIVE EMBODIMENTS

Figure 1:
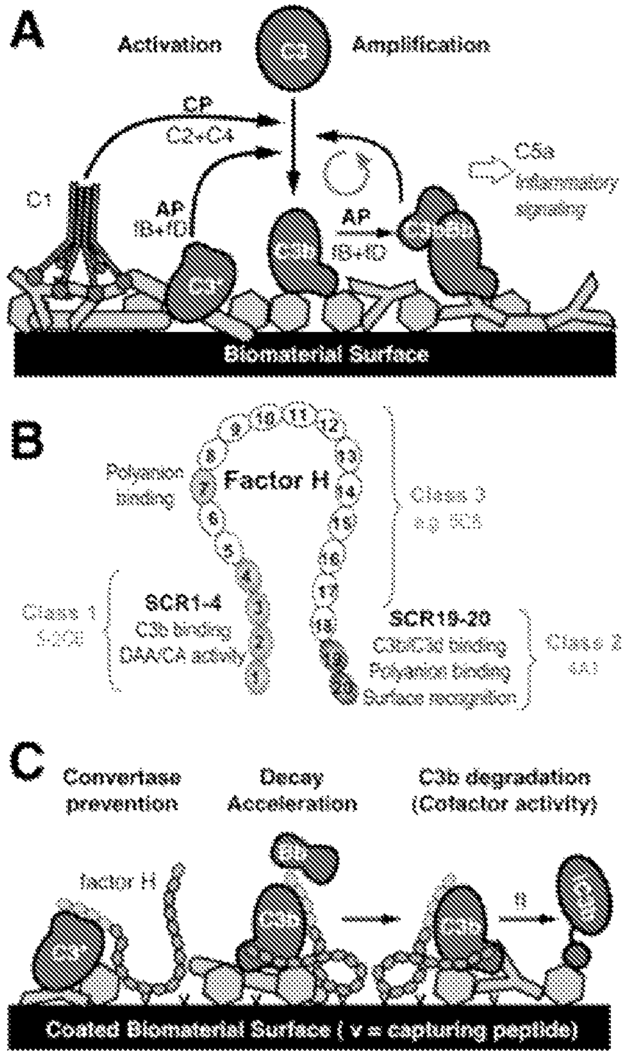
FIG. 1. Schematic representation of biomaterial-induced complement activation and its prevention by factor-H binding peptides. (A) Initiation of the complement cascade by adsorbed plasma proteins (light grey) via the CP or AP, and AP-driven amplification of the response that leads to attaction of immune cells and pro-inflammatory signaling. (B) Domain organization of factor H with SCR domains involved in regulatory activity, C3b binding or polyanion recognition marked in grey. The major binding areas of the three peptide classes are indicated by brackets. (C) Proposed mechanism of biomaterial surface protection by factor H-capturing peptides. Immobilized capturing entities (v) recruit factor H via binding to its non-regulatory domains, thereby enabling active regulation of convertase activity on the modified surface.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, protein chemistry and nucleic acid chemistry and hybridization are those well known and commonly employed in the art.

Abbreviations that may be used herein are as follows: AP, alternative pathway of complement activation; C4BP, C4-binding protein; CP, classical pathway of complement activation; DCM, dichloromethane; DIC, diisopropylcarbodiimide; DMF, dimethylformamide; fH, factor H; fI, factor I; Fmoc, fluorenylmethyloxycarbonyl; GAG, glycosaminoglycans; HOAt, 1-hydroxy-7-aza-benzotriazole; HSA, human serum albumin; LC, linear compstatin; LP, lectin pathway of complement activation; NHS, normal human serum; PEG, polyethylene glycol; RCA, regulator of complement activation; RT, room temperature; RU, resonance units; SCR, short consensus repeat domain; SPR, surface plasmon resonance; TFA, trifluoroacetic acid; TIPS, triisopropylsilane; VBS, veronal buffered saline.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"Treating" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by a patient. "Treating" can also refer to reducing or eliminating a condition of a part of the body, such as a cell, tissue or bodily fluid, e.g., blood.

"Preventing" refers to the partial or complete prevention of the disease or condition in an individual or in a population, or in a part of the body, such as a cell, tissue or bodily fluid (e.g., blood). The term "prevention" does not establish a requirement for complete prevention of a disease or condition in the entirety of the treated population of individuals or cells, tissues or fluids of individuals.

The term "treat or prevent" is sometimes used herein to refer to a method that results in some level of treatment or amelioration of the disease or condition, and contemplates a range of results directed to that end, including but not restricted to prevention of the condition entirely.

A "prophylactic" treatment is a treatment administered to a subject (or sample) who does not exhibit signs of a disease or condition, or exhibits only early signs of the disease or condition, for the purpose of decreasing the risk of developing pathology associated with the disease or condition. This term may be used interchangeably with the term "preventing," again with the understanding that such prophylactic treatment or "prevention" does not establish a requirement for complete prevention of a disease in the entirety of the treated population of individuals or tissues, cells or bodily fluids.

As used herein, a "therapeutically effective amount" or simply an "effective amount" is the amount of a composition sufficient to provide a beneficial effect to the individual to whom the composition is administered, or who is otherwise treated using a method involving the composition.

The term "extracorporeal treatment" as used herein refers generally to treatment or manipulation of cells, tissues or bodily fluids that have been removed from an individual and are thereafter returned to the same individual or to another individual. Examples of extracorporeal treatments include, but are not limited to, extracorporeal shunting of blood during surgical procedures, for example, hemodialysis, and cell or tissue transplantation, to name a few.

The term "biomaterials" as used herein refers to components of equipment, devices or articles that come into contact with, biological substances such as cells, tissues or biological fluids, such as those being subjected to the extracorporeal treatment, or tissues surrounding an implanted device or tissue, such as stents, tubes, artificial tissues or other implants.

It is understood that any and all whole or partial integers between any ranges set forth herein are included herein.

As used herein "comprising" is to be interpreted as specifying the presence of the stated features, integers, steps, or components as referred to, but does not preclude the presence or addition of one or more features, integers, steps, or components, or groups thereof. Thus, for example, a container comprising one tab may have two or three tabs. Additionally, the term "comprising" is intended to include embodiments encompassed by the terms "consisting essentially of" and "consisting of:" Similarly, the term "consisting essentially of" is intended to include embodiments encompassed by the term "consisting of"

DESCRIPTION

The present invention springs in part from the inventors' identification of novel factor H-binding peptides that binds to a region of factor H that does not impede the complement-inhibitory activity of the factor. When immobilized onto the surface of a biomaterial, these peptides recruit factor H, resulting in a substantial inhibition of biomaterial-induced complement activation in a biological substance exposed to the biomaterial.

Peptides:

As mentioned above, the peptides identified in accordance with the present invention are capable of binding factor H without impeding its ability to inhibit complement activation. In certain embodiments, the complement inhibitory activity of factor H includes down-regulating the alternative pathway (AP) of complement activation, in particular by inhibiting formation of the AP C3 convertase. In particular, the peptides do not impede activities attributed to known regions of factor H, including SCR 1-4, 19 and 20, as described and shown in FIG. 1. Thus, in certain embodiments, the peptides bind factor H in one or more of SCR 5-18.

The factor H-binding peptides of the invention are preferably small, i.e., fewer than about 20 amino acid residues in length, or in certain embodiments, fewer than 19, 18, 17, 16, 15, 14, 13, 12, 11 or 10 amino acids in length. In certain embodiments, the peptides comprise the consensus sequence: Cys-Xaa1-Tyr-Xaa7-Xaa3-Trp-Cys-Xaa4-His (SEQ ID NO:1) wherein the peptide is a cysteine cyclic peptide, and Xaa1 is any amino acid; Xaa2, is Asp or Ser; Xaa3 is His or Tyr; and Xaa4 is any amino acid;

In other embodiments, the peptide can be represented by the formula Z—U, wherein Z and U are joined by a peptide bond and wherein U is the consensus sequence described above and Z is a peptide comprising: Ala-Ser-Xaa5-Xaa6-Xaa7 (SEQ ID NO:2), wherein Xaa5 is Ser or Pro, Xaa6 is absent or is any amino acid; and Xaa7 is absent or is any amino acid. As described in detail herein, certain embodiments may comprise a more specific selection of amino acids. For instance: Xaa1 can be Thr, Ser, Asp or Met; Xaa4 can be Ser, Arg, Leu, Ala or Thr; Xaa6 can be Ser, Phe or Asn; and/or Xaa7 can be Arg, Trp, Lys or Val. Particular sequences include:

```
                        (SEQ ID NO: 3)
ASSSRCTYDHWCSH;

                        (SEQ ID NO: 4)
ASPSWCSYSHWCRH;

                        (SEQ ID NO: 5)
ASSFKCDYSHWCLH;

                        (SEQ ID NO: 6)
ASSNVCSYSYWCAH;
and

                        (SEQ ID NO: 7)
ASSCMYSYWCTH.
```

The factor H binding peptides of the present invention may be prepared by various synthetic methods of peptide synthesis via condensation of one or more amino acid residues, in accordance with conventional peptide synthesis methods. For example, peptides are synthesized according to standard solid-phase methodologies, such as may be performed on an Applied Biosystems 433A peptide synthesizer using Fast-Moc chemistry (Applied Biosystems, Foster City, Calif.), according to manufacturer's instructions. Other methods of synthesizing peptides or peptidomimetics, either by solid phase methodologies or in liquid phase, are well known to those skilled in the art. During the course of peptide synthesis, branched chain amino and carboxyl groups may be protected/deprotected as needed, using commonly-known protecting groups. An example of a suitable peptide synthetic method is set forth in Example 1. Modification utilizing alternative protecting groups for peptides and peptide derivatives will be apparent to those of skill in the art.

Alternatively, certain peptides of the invention may be produced by expression in a suitable prokaryotic or eukaryotic system. For example, a DNA construct may be inserted into a plasmid vector adapted for expression in a bacterial cell (such as *E. coli*) or a yeast cell (such as *Saccharomyces cerevisiae*), or into a baculovirus vector for expression in an insect cell or a viral vector for expression in a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The peptides can also be produced by expression of a nucleic acid molecule in vitro or in vivo. A DNA construct encoding a concatemer of the peptides by modifying the termini to contain a cleavable linkage (e.g., adding or substituting Gly at the N-terminus and Asn at the C-terminus), the upper limit of the concatemer being dependent on the expression system utilized, may be introduced into an in vivo expression system. After the concatemer is produced, cleavage between, e.g. the C-terminal Asn and the following N-terminal G is accomplished by exposure of the polypeptide to hydrazine.

The peptides produced by gene expression in a recombinant procaryotic or eucaryotic system may be purified according to methods known in the art. A combination of gene expression and synthetic methods may also be utilized to produce analogs of the above-described factor H-binding peptides. For example, an analog can be produced by gene expression and thereafter subjected to one or more post-translational synthetic processes, e.g., to modify the N- or C-terminus or to cyclize the molecule.

In certain embodiments, the factor H-binding peptides are adapted to include a linker or other modification to facilitate attachment to a solid surface, such as the surface of a biomaterial. Use of linkers to immobilize peptides on solid surfaces is well known in the art. One such modification comprisese biotinylation. Biotinylated factor-H binding peptides are particularly useful in the invention, as they may be conveniently linked to streptavadin-coated biomaterials. Methods of biotinylating peptides are well known in the art. A suitable method is described herein in Example 2.

Other peptide modifications useful for immobilizing peptides to biomaterials include, but are not limited to: (1) addition/substitution of a free sulfhydryl group or a terminal cysteine, which may be linked to substrates that have been activated with a thioester component (e.g., via treatment with SulfoLink® Coupling Gel (Thermo Fisher Scientific, Rockford Ill.); and/or (2) construction of chimeric molecules comprising a portion that binds to cells and another portion that binds to factor H. The cell-binding portion may be specific to particular cells, or they may be non-specific, e.g., capable of insertion into a lipid membrane.

Biomaterials Treated with Factor H-Binding Peptides:

Another aspect of the invention features a composition comprising a factor-H binding peptide affixed to a biomaterial. The biomaterial can be any material to which biological substances in which complement activation occurs is exposed. Non-limiting examples of biomaterials include: (1) plastics and polymers, such as are used in tubing, filters and various implantable devices; (2) metals, such as may be used in implantable devices, (3) ceramics, such as may be used in a variety of devices; (4) artificial tissues, including biomatrices that support cell growth, (5) living tissues and organs (e.g., for transplantation or cell-based therapies); (6) liposomes; (7) polymers; (8) composite materials; and (9) nanoparticles.

Depending on the biomaterial, the factor H-binding peptides may be affixed directly or indirectly to the biomaterial. A person of skill in the art is able to determine whether direct or indirect attachment of a peptide to a biomaterial is preferred. Examples of biomaterials to which the peptides may be directly affixed include certain artificial tissues, and living tissues and organs. Examples of biomaterials to which the peptides may be affixed via a linker or similar modification include plastics, polymers, metals and ceramics. In this latter embodiment, several linker systems are known in the art, as alluded to above. These include, but are not limited to: (1) avidin-biotin; (2) thioester-sulthydryl; and/or (3) chimeric molecules, as described above.

In certain embodiments, the factor H-binding peptides are substantially irreversibly affixed to the biomaterial. In other embodiments, the peptides may be reversibly affixed to the biomaterial, such that a later treatment of the material can release the peptides from the biomaterial.

In some embodiments, the biomaterial to which the factor H-binding peptides have been affixed may be pre-coated with factor H as well. Such biomaterials may be useful, for example, for implantation or transplantation of biomaterials into substantially solid tissues or organs, where in situ recruitment of factor H could be limited.

Methods:

Another aspect of the invention features a method of reducing complement activation in a biological substance that is exposed to a biomaterial. Typically, the method comprises: (1) affixing factor H-binding peptides to the biomaterial, as described above; and (2) exposing the biological substance to the factor H-binding peptide-coated biomaterial. This method is particularly suitable for biological substances that intrinsically contain factor H that can be recruited to the factor H-binding peptides coated onto the biomaterial, and thereby effect an autologous reduction in complement activation. Such biological substances include, but are not limited to, blood and components thereof, such as plasma and serum, lymph, intramuscular fluids, tissues and organs (e.g., liver among others).

In other embodiments, it may be useful to pre-coat the factor H-binding peptide-coated biomaterial with factor H. As mentioned above, this additional step may be advantageous in cases where the factor H present in the biological substance is not easily accessible to the peptide-coated biomaterial. Biological substances in which this may be the case include, for instance, solid tissues or organs. Suitable sources of factor H for use in this pre-coating step, if needed, include factor H obtained from same patient, or from a different individual, or produced by synthetic means, or by recombinant means. In one embodiment, the factor H is obtained from the same patient, e.g., by exposing the peptide-coated biomaterial to an aliquot of the patient's own blood, prior to exposing the biomaterial to the biological substance.

The following examples are provided to describe the invention in greater detail. They are intended to illustrate, not to limit, the invention.

Example 1

This example describes the identification factor H binding peptides that bind factor H without compromising the complement-inhibitory and cell-binding activities of factor H.

Materials and Methods:

Complement Components and Recombinant Proteins.

Human factor H was purified from normal human serum (NHS) by 5-12% PEG precipitation. The pellet was resuspended in 3 mM $KH_2PO_4$, 50 mM NaCl, pH 7.4, and the sample was injected onto a Source Q column (GE Healthcare). The protein was eluted using a step gradient with increasing salt concentrations. Fractions containing factor H were identified by direct ELISA using rabbit anti-human factor H polyclonal antibody (raised by standard procedures) followed by HRP-conjugated goat anti-rabbit IgG (Bio-Rad), pooled, dialyzed and subsequently injected onto a Mono-S column (GE Healthcare). The eluted samples were identified by SDS-PAGE analysis, pooled and dialyzed against PBS, pH 7.4. Human complement C3 was purified from NHS according to known methods. C3b was generated by limited trypsin digestion on an activated thiol-Sepharose 4B column (GE Healthcare) and eluted with 20 mM L-cysteine. The eluted protein was treated with 100 mM iodoacetamide and further purified on a Mono-Q column (GE Healthcare). The expression and purification of factor H SCR 1-4 (referred to as "fH1-4" here) have been described (Wu, J et al., 2009, supra) Factor I and fH19-20 were obtained from other sources Phage-Displayed Peptide Libraries and Biopanning of Phage Libraries.

To discover factor H-binding peptides, we screened two variable cysteine-constrained phage-displayed libraries (ANL4, ANL5). Factor H-binding phage clones were isolated through three rounds of library screening. In the first round, microliter wells (Nunc Inc., Naperville, Ill.) were coated overnight with factor H (5 μg per well) or BSA (20 μg per well) in PBS at 4° C. and saturated with 5% non-fat milk in PBS for 1 h at room temperature (RT). After washing, the libraries were prescreened by incubating $2\times10^{12}$ plaque-forming units of each library in BSA-coated wells for 1 h at RT; supernatants were then transferred to factor H-coated wells for binding at RT for 2 h. The wells were washed six times with PBST buffer (PBS with 0.1% Tween-20), and bound phage particles were eluted with 0.2 M glycine, pH 2.2, and immediately neutralized with 1 M Tris-HCl, pH 9.1. Recovered phage particles were amplified in *E. coli* strain XL1Blue F' $Tet^R$ for the next round of screening; the screening procedure was repeated twice as described above. After the third round, the recovered phage particles were plated for identification by monoclonal phage ELISA.

Monoclonal Phage ELISA.

Microtiter wells were coated overnight with either factor H or BSA at 5 μg/mL in PBS at 4° C., and saturated with 5% non-fat milk in PBST for 1 h. Completely separated individual phage plaques from the third round of screening were picked and amplified. Phage particles of each amplified individual phage plaque were added to both factor H- and BSA-coated wells in parallel and allowed to bind at RT for 1 h. After six washes with PBST, bound phages were detected with HRP-conjugated anti-M13 monoclonal antibody (GE Healthcare), using ABTS (Roche) for color development. Clones that bound to factor H but not to BSA were considered positive; single-stranded DNA from positive clones was prepared using an M13 kit (Qiagen, Valencia, Calif.) and sequenced by the DNA sequencing facility of the University of Pennsylvania.

To localize the binding sites on factor H of the positive clones, we further tested each clone by monoclonal phage ELISA for binding to factor H and its N- and C-terminal fragments, i.e. fH1-4 and fH19-20.

Results:

Combinatorial peptide libraries are a rich source of structural diversity, and the screening of such libraries has proven to be an effective strategy for identifying peptide ligands to target proteins. To isolate factor H-binding phage peptides, we screened two variable cysteine-constrained phage-displayed peptide libraries, ANL4 and ANL5, each containing about 2×1010 unique clones. A prescreening step was performed to eliminate potential non-specific binding phages, e.g., those that bind to plastic. After the third round of screening, we tested 96 individual clones from each library by monoclonal phage ELISA for their ability to bind factor H; 24 positive clones from each library were identified and sequenced.

Figure 2:
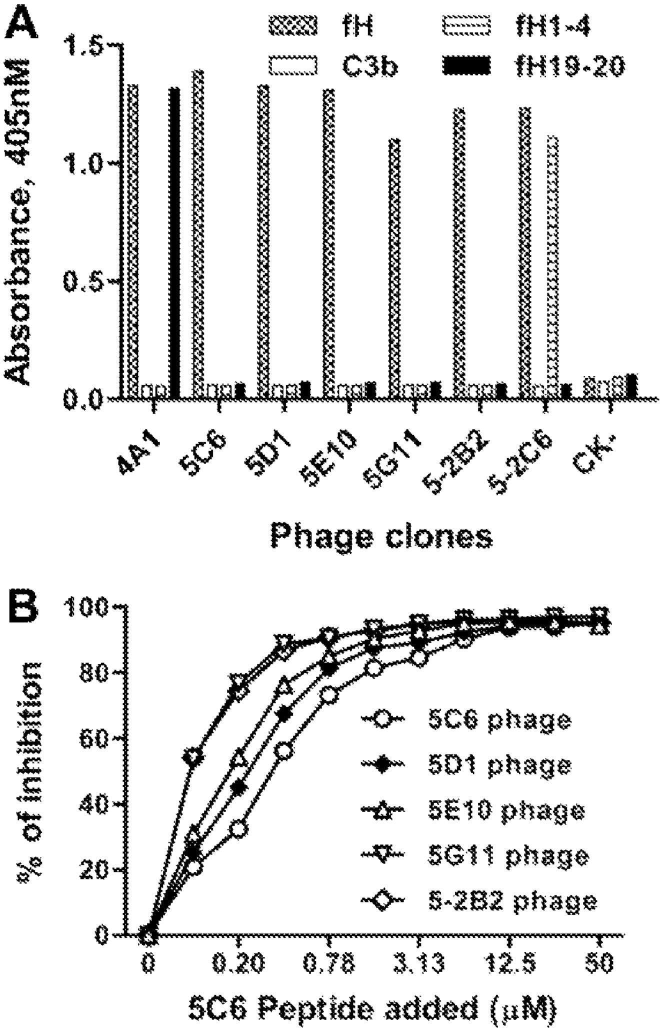
FIG. 2. Specificity characterization of factor H-binding phage clones. (A) Major binding areas of positive clones on factor H were eludicated by monoclonal phage ELISA. Each clone was tested for binding to factor H, its N/C-terminal fragments fH1-4 and fH19-20, and C3b (negative control). (B) Binding of all class 3 clones (Table 1) to a common area on SCR5-18 as confirmed by strong competition with the 5C6 peptide for binding to factor H. Data are representatives of three separate experiments showing similar results.

All sequenced positive clones from library ANL4 were found to have identical sequence (class 1; clone 4A1; Table 1) and bind to the C-terminal two SCR of factor H (i.e. fH19-20; FIG. 2A). From library ANL5, we identified six clones with unique sequences (Table 1).

TABLE 1

Phage display screening-derived factor H-binding peptides

| Class[1] | Phage Library | Phage clone | Peptide sequence | Seq. ID NO: | Binding area on factor H[2] |
|---|---|---|---|---|---|
| 1 | ANL4 | 4A1 | ASSGMCFTKKTVLC | 8 | SCR19-20 |
| 2 | ANL5 | 5-2C6 | ASSYDVGYSHDCRF | 9 | SCR1-4 |
| 3 | ANL5 | 5C6 | ASSSRCTYDHWCSH | 3 | SCR5-18 |
| | ANL5 | 5D1 | ASPSWCSYSHWCRH | 4 | SCR5-18 |
| | ANL5 | 5E10 | ASSFKCDYSHWCLH | 5 | SCR5-18 |
| | ANL5 | 5G11 | ASSNVCSYSYWCAH | 6 | SCR5-18 |
| | ANL5 | 5-2B2 | ASSCMYSY--WCTH | 7 | SCR5-18 |
| Control Peptide (LC)[3] | | | IAVVQDWGHHRAT | 10 | N/A |

[1]Peptide class based on binding site region on factor H.
[2]Determined by monoclonal phage ELISA. The SCR5-18 area was attributed in absence of stable binding to either the N- or C-terminus of factor H..
[3]Linear compstatin (Cys-to-Ala double mutant).

One of the clones, 5-2C6, bound to the N-terminal regulatory region of factor H (i.e., fH1-4; class 2) whereas the remaining clones did not show significant binding to any of the terminus fragments (class 3); these clones therefore likely have a major binding site in the wide middle region of factor H between SCR5 and 18 (FIG. 2A). Neither 4A1 nor 5-2C6 was considered for subsequent experiments as they may potentially interfere with either the C3b binding or the regulatory activity of factor H. Therefore, we focused on the further characterization of the rest of the positive clones from ANL5. Sequence alignment showed a consensus sequence of xCxY[S/D][Y/H]WC×H (SEQ ID NO:11) among these clones (Table 1), suggesting that their binding sites on factor H are overlapping or even identical.

Example 2

This example sets forth a demonstration that certain of the peptides identified as described in Example 1 are capable of binding factor H without compromising the complement-inhibitory and cell-binding activities of factor H, and can be immobilized onto biomaterials.

Materials and Methods:

Peptide Synthesis.

$N^{\alpha}$-Fmoc-amino acids, PyBOP and Rink amide MBHA resin (0.34 mmol/g) were obtained from Novabiochem (San Diego, Calif.). DIC was purchased from AnaSpec (San Jose, Calif.). HOAt was purchased from Advanced ChemTech (Louisville, Ky.). HSW syringes (Torviq, Niles, Mich.) (10 ml) with frits on the bottom were used for all peptide syntheses. Dichloromethane (DCM) and N-methylpyrrolidinone were obtained from Fisher Scientific. All other chemical reagents for synthesis were purchased from Sigma-Aldrich (St Louis, Mo.) and used without further purification.

The N-terminal Fmoc protected linear peptides used in this study were synthesized on an Applied Biosystems 433A peptide synthesizer using FastMoc chemistry. Linear peptides were cyclized manually on resin in an HSW polypropylene syringe using thallium acetate in DMF/anisole (19:1, RT, 3 h). To couple biotin to the cyclized peptides, the C-terminal lysine side chain Mmt protecting group was selectively removed in 1% TFA (with 5% TIPS as scavenger). The coupling was then carried out in N-methyl-2-pyrrolidone using PyBOP and HOAt until a negative Kaiser test result was observed. After removal of the Fmoc protecting group, the resin was washed with DCM (4×5 ml), then DCM/diethylether (1:1.4×5 ml) and dried under a vacuum for 4 h. The peptides were cleaved from the resin with a mixture of 95% TFA, 2.5% water and 2.5% TIPS for 3 h. After evaporation of the TFA under vacuum, the peptides were precipitated and washed three times with 5 ml each of cold diethyl ether. The liquid was separated from the solid by centrifugation and was decanted. The crude peptides were dried in air and dissolved in acetonitrile and 0.1% TFA in water (1:1) before purification by preparative reversed-phase HPLC to >95% purity.

Analytical HPLC was performed on a Waters Autopurification. System using an XBridge BEH130 C18 column (Waters, Milford, Mass.). Preparative HPLC was performed on a Waters Autopurification System using a Waters XBridge BEH130 Prep C18 OBD column. Mass spectra were obtained online using a Waters MICROMASS ZQ 4000 mass spectrometer or separately on a Waters MALDI micro MX.

Peptide Binding to Factor H.

Two approaches were used to evaluate the binding of synthetic peptides to factor H. First, we used peptide-phage competition assays, in which serially diluted synthetic peptide was added to its parent phage at the step of phage binding to coated factor H. The rest of the steps were performed as described above for monoclonal phage ELISA. Second, ELISA experiments were used to evaluate the binding of factor H to the immobilized peptide. Microtiter plates were coated with streptavidin (New England Biolabs) at 10 μg/ml in PBS at 4° C. overnight, and saturated with 2% BSA in PBS. After washing, either the biotinylated 5C6 peptide or a biotinylated control peptide (linear compstatin; IAVVQDWGHHRAT; SEQ ID NO:10) was added at 10 μg/ml and allowed to bind at RT for 30 min. The wells were washed again, and factor H serially diluted in PBS, starting with 2.5 μg/ml, was added. After 1 h of binding, the plates were washed, and bound factor H was detected with goat anti-human factor H polyclonal antibody (Quidel, San Diego, Calif.), followed by HRP-conjugated rabbit anti-goat IgG (Bio-Rad). In an alternative approach, human plasma that was anticoagulated with the thrombin inhibitor lepirudin (Refludan™, Behring GmbH Marburg Germany; final concentration 50 μg/ml), serially diluted in veronal-buffered saline, pH 7.4 containing 0.15 mM $Ca^{2+}$ and 0.5 mM $Mg^{2+}$ (VBS), was used instead to assess the capture of factor H from plasma by the immobilized peptide.

Cofactor Activity Assays and Hemolytic Assays.

To determine whether the binding of the 5C6 peptide interferes with the regulatory activity and cell-surface binding capacity of factor H, we performed factor H cofactor activity assays using purified C3b, factor H and factor I, as well as hemolytic assays, both which were performed in the presence of different concentrations of the 5C6 peptide. The hemolysis assay experiments were repeated at least three times using lepirudin plasma from different blood donors.

Cofactor Activity Assay:

The factor H cofactor activity assay was performed according to known methods. In brief, 1.14 μM C3b, 16 nM factor I, and 72 nM factor H were incubated with various amounts of the 5C6 peptide (0.4, 4, and 40 μM, respectively) in PBS at 37° C. for 1 hr in a final volume of 20 μl. The reaction was terminated by adding SDS-PAGE loading buffer, and the samples were analyzed by 8% SDS-PAGE under reducing conditions, followed by Coomassie blue staining.

Hemolytic Assay:

Hemolytic assays were performed to determine whether the peptide altered factor H cell-surface binding activity. Sheep erythrocytes (Cocalico Biological Inc., Reamstown, Pa.) were washed with VBS containing 5 mM $Mg^{2+}$/EGTA (VBS-$Mg^{2+}$/EGTA) until the supernatant was clear. The assay was titrated by lysing erythrocytes in serial dilution with water in a final volume of 300 μl. The $OD_{405}$ of the supernatants was measured, and the amount of the erythrocytes yielding an $OD_{405}$ of ~1 was used in the assay. Serial dilutions of the 5C6 peptide or monoclonal antibody MH10 (which binds fH19-20 and inhibits factor H cell surface binding) with the determined amount of sheep erythrocytes and lepirudin plasma diluted 1:10 in VBS-$Mg^{2+}$/EGTA in a final volume of 300 μL were incubated at 37° C. for 1 h in a shaking water bath. After centrifugation the $OD_{405}$ of the supernatants was measured, and the OD value was used to represent the cell lysis.

Interaction Analysis of Factor H to Immobilized Peptide 5C6.

The binding of factor H with surface-bound 5C6 peptide was further characterized using surface plasmon resonance (SPR) on a ProteOn XPR36 instrument (Bio-Rad Inc., Hercules, Calif.) using PBST (10 mM sodium phosphate, 150 mM NaCl, 0.005% Tween 20) as running buffer. Streptavidin (50 μg/ml in 10 mM sodium acetate pH 5.0) was immobilized on a GLC sensor chip at 30° C. using amine coupling. The biotinylated 5C6 peptide and a biotinylated control peptide (linear compstatin; see above) were captured on separate streptavidin-coated channels to a density of ~200 resonance units (RU). Purified factor H (Complement Technologies, Tyler, Tex.) or recombinant fragments fH1-4 and fH19-20 were injected at a concentration of 100 nM for 2 rain at a flow rate of 25 μl/min with a dissociation phase of 6 min. A single injection of 2 M NaCl for 30 s was used to regenerate the surface between injections. Data were processed using ProteOn Manager software by subtracting the signals from interspots and a blank streptavidin channel. In order to estimate the apparent binding affinity, a twofold dilution series of factor H (0.24-500 nM) was injected using the same protocol and fitted to various kinetic models using ProteOn Manager. In order to exclude sensor chip matrix-specific surface binding, the same experiment was repeated on Biacore 3000 instrument (GE Healthcare) using a SA chip under the same conditions as described above.

Inhibition of Biomaterial-Induced AP Activation by Immobilized Peptide.

Polystyrene microtiter wells, which served as a model biomaterial, were coated overnight with streptavidin (10 μg/ml in PBS) at 4° C. After washing, the biotinylated 5C6 peptide and the control peptide (10 μg/ml in PBS) were added to the wells and incubated at RT for 30 min. The wells were again washed and serially diluted lepirudin plasma in VBS-$Mg^{2+}$/EGTA was added and incubated at RT for 1 h. In some experiments intended to monitor the inhibition of AP by immobilized peptide on a HSA monolayer, the washed wells were saturated with 2% HSA in PBS for 1 h, prior to the addition of plasma. In both series of experiments, the wells were then washed, and the binding sites were saturated with 2% BSA in PBS for 1 h. Bound fragments of activated C3 were detected with an HRP-conjugated goat anti-human C3 polyclonal antibody (Cappel, Aurora, Ohio). In parallel, captured factor H from serum was detected with goat anti-human factor H polyclonal antibody followed by HRP-conjugated rabbit anti-goat IgG in duplicate wells as described above.

Results:

Synthetic 5C6 peptide directly binds factor H with high affinity.

Clone 5C6 was selected for further evaluation and the corresponding peptide was prepared using solid-phase peptide synthesis. To confirm that the synthetic peptide binds factor H the same way as the parent phage does, we conducted a peptide-phage competition experiment in which the peptide, if active, would prevent the parent phages to bind factor H. Indeed, the 5C6 peptide inhibited its parent phages from binding to factor H in a dose-dependent manner (FIG. 2B), indicating that the synthetic peptide bound to same site on factor H as its parent phages. In addition, the 5C6 peptide also strongly inhibited the rest of the phages in this category from binding to factor H in a similar dose-dependent manner (FIG. 2B), thereby supporting the hypothesis that their binding sites on factor H are overlapping or identical (see above).

The direct binding between the peptide and factor H was initially evaluated in an ELISA experiment, in which the biotinylated 5C6 peptide and a biotinylated control peptide of similar size and charge (i.e., linear compstatin) were captured by coated streptavidin and the binding of purified factor H was detected by polyclonal antibodies. A strong binding signal for factor H was observed in wells with immobilized 5C6 peptide, but not in wells bearing the control peptide (FIG. 3A), thereby confirming a direct capturing of factor H by the peptide.

Figure 3:
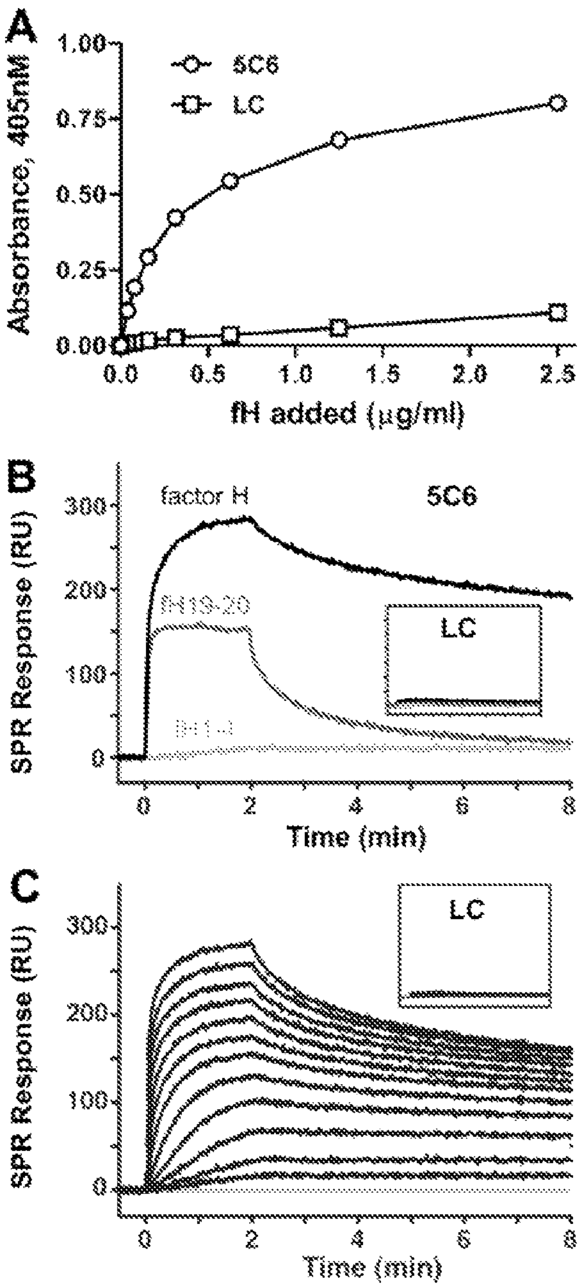
FIG. 3. Binding of factor H to surfaces coated with synthetic 5C6 peptide as assessed by ELISA (A) and SPR (B-C). (A) Polystyrene wells were coated with streptavidin, saturated with BSA, and incubated with biotinylated 5C6 peptide or negative control peptide; following incubation with serially diluted factor H, bound factor H was detected by a polyclonal antibody. Data shown are means±SD (within the symbols) from a representative of three experiments. (B, C) Biotinylated 5C6 peptide or control (LC, inserts) were captured on streptavidin-coated SPR sensor chips, and factor H fragments at a fixed concentration (100 nM; B) or a dilution series of factor H (0.24-500 nM; C) were injected for 2 min with a dissociation phase of 6 min. Shown data are representatives of two independent experiments on different SPR instruments showing comparable results.

The binding activity and specificity was further validated using SPR assays, by simultaneously injecting factor H or its fragments over biotinylated 5C6 peptide and the control peptide, which were captured on a streptavidin-coated sensor chip. In agreement with the ELISA, the 5C6 peptide showed a high binding activity and stability for factor H whereas no significant binding was observed on the control surface (FIG. 3B and insert). While a significant SPR response could also be detected for the fH19-20 fragment, this interaction was not stable and the signal rapidly returned to baseline. Importantly, no binding of the regulatory fH1-4 fragment could be observed under the same conditions (FIG. 3B). Together, these results indicate that the middle region likely mediates the stable capturing of full-length factor H. Screening of a dilution series of factor H (0.24-500 nM) revealed concentration-dependent binding with high affinity, yet the kinetic evaluation showed a significant deviation from a single-site model (FIG. 3C and Supplemental Material). Although the SPR results were closely comparable between two different SPR instruments featuring distinct surface chemistries (alginate versus carboxymethyl dextran matrix; data not shown), the observed binding pattern and affinities are nevertheless likely to be largely influenced by surface properties (peptide density, surface charges, etc.) and have to be regarded as apparent effects under the given conditions. Overall, however, the SPR results clearly confirmed a direct and specific binding of factor H to surface-immobilized peptide 5C6 as observed in ELISA.

The 5C6 Peptide does not Interfere with Factor H Activity.

Figure 4:
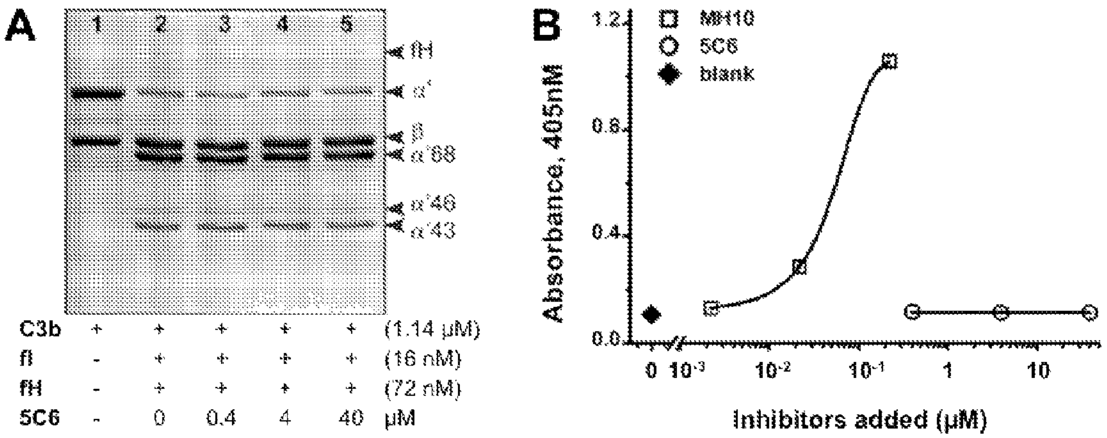
FIG. 4. Maintenance of the functional integrity of factor H in the presence of 5C6 peptide. (A) The effects of the 5C6 peptide on the factor I-mediated cleavage of C3b (cofactor activity) was tested using a solution cleavage assay and analyzed by SDS-PAGE: lane 1, C3b; lanes 2-5, C3b, factor H, factor I and increasing concentrations of 5C6 peptide (0-40 μM). (B) Effect of 5C6 peptide on surface recognition by factor H as measured in a hemolytic assay in the presence of increasing concentrations of either the 5C6 peptide or a monoclonal antibody against SCR19-20 of factor H (MH10). Data are means±SD from a representative of three experiments.

In order to inhibit the activation of complement, factor H recruited by the 5C6 peptide immobilized on a biomaterial surface must retain its regulatory activities. To confirm that this was the case, we first assayed the cofactor activity of factor H for the factor I-mediated degradation of C3b in the presence of increasing concentrations of the 5C6 peptide. As expected, 5C6 did not inhibit factor H cofactor activity, even at a 550-fold excess (40 μM) over factor H (72 nM) (FIG. 4A).

Next, we performed hemolytic assays to determine whether the 5C6 peptide influenced the cell-surface binding of factor H. Sheep erythrocytes are known for their strong binding to human factor H, and are often used to evaluate the effect of cell-surface binding on human factor H activity. No lysis of sheep erythrocytes mixed with 10-fold diluted lepirudin plasma was seen in the presence of the 5C6 peptide up to a concentration of 40 μM (FIG. 4B). In contrast, the presence of the monoclonal antibody MH10 recognizing the C-terminus of factor H, induced quantitative cell lysis at a concentration of 0.2 μM, most likely due to inhibited factor H cell-surface binding (FIG. 4B). Taken together, these results indicate that the 5C6 peptide does not interfere with the co-factor activity or cell-surface binding properties of factor H.

When expressed as fusion proteins with phage PIII domain, the peptides that bound to either the N-terminus (i.e., 5-2C6) or C-terminus of factor H (i.e., 4A 1) affected the cofactor and hemolytic assays, respectively, while no such effect was observed for the 5C6 fusion protein (not shown). Whereas this suggests that class 1 and 2 peptides are less feasible for functional capturing of factor H, they may serve as interesting lead structures for developing important tools in complement research.

Inhibition of Biomaterial-Induced AP Activity by the Immobilized 5C6 Peptide.

In order to prevent biomaterial-induced complement activation, the surface-coated 5C6 peptide must be able to functionally capture factor H from circulation even in presence of a plasma protein layer. To test this capability, we first assessed the complement-inhibitory capacity of the 5C6 peptide on a model biomaterial surface (polystyrene) carrying a HSA monolayer. After capture of the biotinylated peptide by coated streptavidin, the microtiter wells were saturated with 2% HSA. The major purpose of this experiment was to ascertain that the conjugated peptide would not be masked by the initial protein film, consisting mainly of HSA, which is rapidly adsorbed on a surface that is exposed to human blood.

Figure 5:
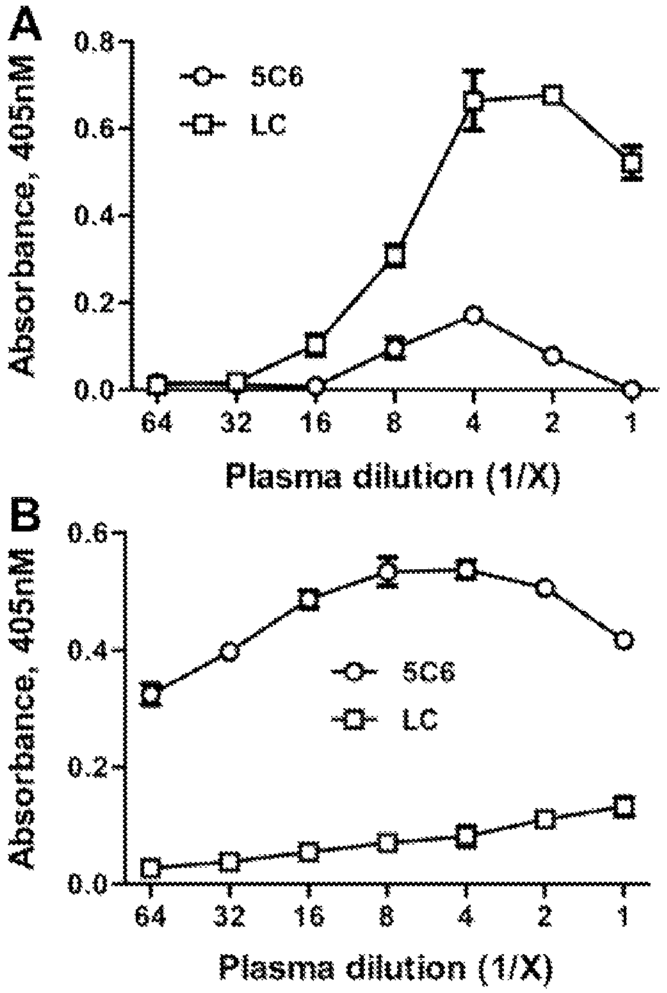
FIG. 5. Inhibition of complement activation by immobilized 5C6 on a polystyrene surface carrying a HSA layer. Biotinylated 5C6 and the control peptide (LC) were captured by coated streptavidin. After being saturated with HSA, wells were incubated with serially diluted lepirudin human plasma to allow complement activation and factor H binding to occur. Complement activation was detected as surface-bound activated C3 (A), and bound factor H was measured in a duplicate samples (B). Data are means±SD from a representative of three experiments.

Anticoagulated plasma was serially diluted in VBS-$Mg^{2+}$/EGTA and incubated in wells coated with either the 5C6 peptide or the control, followed by detection of deposited C3 activation fragments (i.e., C3b/iC3b) and captured factor H. Complement activation was substantially inhibited on the 5C6 peptide-immobilized surface (FIG. 5B), and there was pronounced factor H capture by immobilized 5C6 peptide, as compared to immobilized control peptide (FIG. 5A). These results demonstrated that the immobilized 5C6 peptide is capable of recruiting factor H from the plasma to the surface, resulting in a concomitant inhibition of complement activation by the AP.

Figure 6:
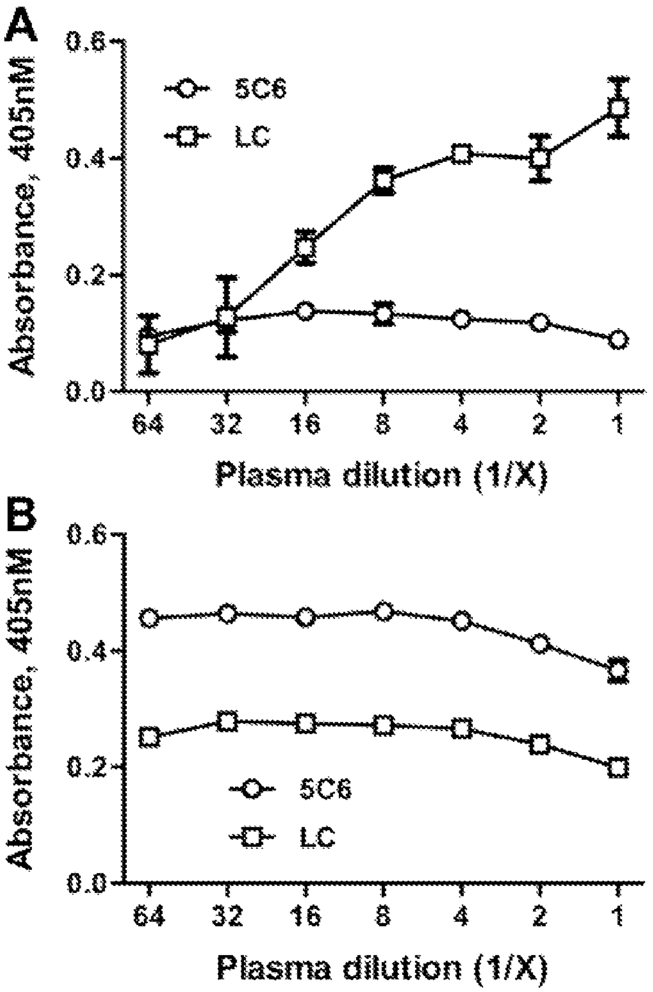
FIG. 6. Inhibition of complement activation by immobilized 5C6 peptide on a polystyrene surface. Biotinylated 5C6 peptide and the negative control peptide (LC) were captured by coated streptavidin. After washing, wells were incubated with serially diluted plasma to allow complement activation and factor H binding to occur and then saturated with BSA. Complement activation was detected as surface-bound activated C3 (A), and bound factor H was measured in a duplicate plate (B). Data are means±SD from a representative of three experiments.

In an effort to mimic the real application more closely, we exposed the peptide-coated polystyrene wells directly to plasma without HSA pre-saturation, thereby allowing formation of a spontaneous and more realistic protein layer. We then assayed for inhibition of complement activation by the 5C6 peptide as described above. Also under these conditions, the immobilized 5C6 peptide captured more factor H from plasma when compared to the control peptide (FIG. 6A), and strongly inhibited complement activation on the surface (FIG. 6B). Importantly, there was no significant decline in factor H concentration in plasma that had been incubated on surfaces with immobilized 5C6 peptide (data not shown), thereby indicating that the surface capturing of factor H does not interfere with the regulatory capacity in circulation.

The present invention is not limited to the embodiments described and exemplified above, but is capable of variation and modification within the scope of the appended claims.

What is claimed:

1. A peptide that binds factor H without interfering with a biological activity of factor H, wherein the biological activity comprises inhibiting complement activation; wherein the peptide is Formula I:

Z—U    Formula I:

wherein:

U is a cysteine cyclic peptide comprising: Cys-Xaa1-Tyr-Xaa2-Xaa3-Trp-Cys-Xaa4-His (SEQ ID NO:1) wherein:

Xaa1 is any amino acid;

Xaa2 is Asp or Ser;

Xaa3 is His or Tyr; and

Xaa4 is any amino acid; and

Z is absent or is a peptide comprising: Ala-Ser-Xaa5-Xaa6-Xaa7 (SEQ ID NO:2) wherein:

Xaa5 is Ser or Pro;

Xaa6 is absent or is any amino acid; and

Xaa7 is absent or is any amino acid;

wherein Z, if present, and U are joined by a peptide bond.

2. The peptide of claim 1, wherein the peptide is less than about 20 amino acid residues in length.

3. The peptide of claim 2, wherein the peptide is less than about 15 amino acid residues in length.

4. The peptide of claim 1, wherein Xaa1 is Thr, Ser, Asp or Met.

5. The peptide of claim 1, wherein Xaa4 is Ser, Arg, Leu, Ala or Thr.

6. The peptide of claim 1, wherein Xaa6 is Ser, Phe or Asn.

7. The peptide of claim 1, wherein Xaa7 is Arg, Trp, Lys or Val.

8. The peptide of claim 1, comprising a sequence selected from:

```
                     (SEQ ID NO: 3)
ASSSRCTYDHWCSH;
                     (SEQ ID NO: 4)
ASPSWCSYSHWCRH;
                     (SEQ ID NO: 5)
ASSFKCDYSHWCLH;
                     (SEQ ID NO: 6)
ASSNVCSYSYWCAH;
and
                     (SEQ ID NO: 7)
ASSCMYSYWCTH.
```

9. A composition comprising the peptide of claim 1 affixed to a biomaterial.

10. The composition of claim 9, wherein the biomaterial comprises one or more of polymers, plastics, metals, ceramics, artificial tissues and organs, or living cells, tissues and organs.

11. The composition of claim 9, wherein the peptide is reversibly affixed to the biomaterial.

12. A method of reducing complement activation in a biological substance that is exposed to a biomaterial, the method comprising:

(a) affixing to the biomaterial a peptide that binds factor H without interfering with the ability of the factor H to inhibit complement activation, thereby forming a peptide-coated biomaterial; wherein the peptide is Formula I:

Z—U Formula I:

wherein:

U is a cysteine cyclic peptide comprising: Cys-Xaa1-Tyr-Xaa2-Xaa3-Trp-Cys-Xaa4-His (SEQ ID NO:1) wherein:

Xaa1 is any amino acid;

Xaa2 is Asp or Ser;

Xaa3 is His or Tyr; and

Xaa4 is any amino acid; and

Z is absent or is a peptide comprising: Ala-Ser-Xaa5-Xaa6-Xaa7 (SEQ ID NO:2) wherein:

Xaa5 is Ser or Pro;

Xaa6 is absent or is any amino acid; and

Xaa7 is absent or is any amino acid;

wherein Z, if present, and U are joined by a peptide bond;

(b) contacting the peptide coated biomaterial with factor H, whereupon the factor H is bound to the peptide on the peptide-coated biomaterial, thereby forming a factor H-enriched biomaterial; and (c) exposing the biological substance to the factor H-enriched biomaterial, whereupon the complement activation in the exposed biological substance is reduced in comparison to an equivalent biological substance exposed to an equivalent biomaterial that has not been affixed with the peptide and contacted with the factor H.

13. The method of claim 12, wherein the biological substance contains the factor H, and the contacting is accomplished when the biological substance is exposed to the peptide-coated biomaterial.

14. The method of claim 13, wherein the biological substance is blood or a component of blood.

15. The method of claim 12, comprising performing the contacting before exposing the biological substance to the peptide-coated biomaterial.

16. The method of claim 15, wherein the biological substance is a tissue or organ.

* * * * *

SEQUENCE LISTING

```
<160> NUMBER OF SEQ ID NOS: 11

<210> SEQ ID NO 1
<211> LENGTH: 9
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(4)
<223> OTHER INFORMATION: Xaa is Asp or Ser
<220> FEATURE:
<221> NAME/KEY: VARIANT
<222> LOCATION: (5)..(5)
<223> OTHER INFORMATION: Xaa is His or Tyr
<220> FEATURE:
<221> NAME/KEY: VARIANT
<222> LOCATION: (8)..(8)
<223> OTHER INFORMATION: Xaa is any amino acid

<400> SEQUENCE: 1

Cys Xaa Tyr Xaa Xaa Trp Cys Xaa His
1               5


<210> SEQ ID NO 2
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (3)..(3)
<223> OTHER INFORMATION: Xaa is Ser or Pro
<220> FEATURE:
<221> NAME/KEY: VARIANT
<222> LOCATION: (4)..(4)
<223> OTHER INFORMATION: Xaa is absent or is any amino acid
<220> FEATURE:
<221> NAME/KEY: VARIANT
<222> LOCATION: (5)..(5)
<223> OTHER INFORMATION: Xaa is absent or is any amino acid

<400> SEQUENCE: 2

Ala Ser Xaa Xaa Xaa
1               5


<210> SEQ ID NO 3
<211> LENGTH: 14
<212> TYPE: PRT
<213> ORGANISM: Artificial sequence
<220> FEATURE:
<223> OTHER INFORMATION: synthetic sequence

<400> SEQUENCE: 3

Ala Ser Ser Ser Arg Cys Thr Tyr Asp His Trp Cys Ser His
1               5                   10
```

<210> SEQ ID NO 4
<211> LENGTH: 14
<212> TYPE: PRT
<213> ORGANISM: Artificial sequence
<220> FEATURE:
<223> OTHER INFORMATION: synthetic sequence

<400> SEQUENCE: 4

Ala Ser Pro Ser Trp Cys Ser Tyr Ser His Trp Cys Arg His
1 5 10

<210> SEQ ID NO 5
<211> LENGTH: 14
<212> TYPE: PRT
<213> ORGANISM: Artificial sequence
<220> FEATURE:
<223> OTHER INFORMATION: synthetic sequence

<400> SEQUENCE: 5

Ala Ser Ser Phe Lys Cys Asp Tyr Ser His Trp Cys Leu His
1 5 10

<210> SEQ ID NO 6
<211> LENGTH: 14
<212> TYPE: PRT
<213> ORGANISM: Artificial sequence
<220> FEATURE:
<223> OTHER INFORMATION: synthetic sequence

<400> SEQUENCE: 6

Ala Ser Ser Asn Val Cys Ser Tyr Ser Tyr Trp Cys Ala His
1 5 10

<210> SEQ ID NO 7
<211> LENGTH: 12
<212> TYPE: PRT
<213> ORGANISM: Artificial sequence
<220> FEATURE:
<223> OTHER INFORMATION: synthetic sequence

<400> SEQUENCE: 7

Ala Ser Ser Cys Met Tyr Ser Tyr Trp Cys Thr His
1 5 10

<210> SEQ ID NO 8
<211> LENGTH: 14
<212> TYPE: PRT
<213> ORGANISM: Artificial sequence
<220> FEATURE:
<223> OTHER INFORMATION: synthetic sequence

<400> SEQUENCE: 8

Ala Ser Ser Gly Met Cys Phe Thr Lys Lys Thr Val Leu Cys
1 5 10

<210> SEQ ID NO 9
<211> LENGTH: 14
<212> TYPE: PRT
<213> ORGANISM: Artificial sequence
<220> FEATURE:
<223> OTHER INFORMATION: synthetic sequence

<400> SEQUENCE: 9

Ala Ser Ser Tyr Asp Val Gly Tyr Ser His Asp Cys Arg Phe
1 5 10

<210> SEQ ID NO 10

-continued

```
<211> LENGTH: 13
<212> TYPE: PRT
<213> ORGANISM: Artificial sequence
<220> FEATURE:
<223> OTHER INFORMATION: synthetic sequence

<400> SEQUENCE: 10

Ile Ala Val Val Gln Asp Trp Gly His His Arg Ala Thr
1               5                   10


<210> SEQ ID NO 11
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is any amino acid
<220> FEATURE:
<221> NAME/KEY: VARIANT
<222> LOCATION: (3)..(3)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is Ser or Asp
<220> FEATURE:
<221> NAME/KEY: VARIANT
<222> LOCATION: (6)..(6)
<223> OTHER INFORMATION: Xaa is Tyr or His
<220> FEATURE:
<221> NAME/KEY: VARIANT
<222> LOCATION: (9)..(9)
<223> OTHER INFORMATION: Xaa is any amino acid

<400> SEQUENCE: 11

Xaa Cys Xaa Tyr Xaa Xaa Trp Cys Xaa His
1               5                   10
```